US012667648B2

(12) United States Patent
Roscioli et al.

(10) Patent No.: US 12,667,648 B2
(45) Date of Patent: Jun. 30, 2026

(54) TISSUE REPAIR DEVICE AND MOLDING PROCESS

(71) Applicant: DSM IP Assets B.V., TE Heerlen (NL)

(72) Inventors: Nicholas Roscioli, Phoenixville, PA (US); Julia Innamorato, King of Prussia, PA (US); James Kolb, Exton, PA (US); Rachel Dichter, Philadelphia, PA (US); Damian Heinz, Exton, PA (US)

(73) Assignee: DSM IP ASSETS, B.V. (NL)

( * ) Notice: Subject to any disclaimer, the term of this patent is extended or adjusted under 35 U.S.C. 154(b) by 489 days.

(21) Appl. No.: 18/033,918

(22) PCT Filed: Oct. 29, 2021

(86) PCT No.: PCT/US2021/057303
§ 371 (c)(1),
(2) Date: Apr. 26, 2023

(87) PCT Pub. No.: WO2022/094246
PCT Pub. Date: May 5, 2022

(65) Prior Publication Data
US 2024/0009355 A1      Jan. 11, 2024

Related U.S. Application Data

(60) Provisional application No. 63/107,618, filed on Oct. 30, 2020.

(30) Foreign Application Priority Data

Nov. 24, 2020     (EP) ..................................... 20209383

(51) Int. Cl.
*A61F 2/28*          (2006.01)
*A61F 2/30*          (2006.01)
(Continued)

(52) U.S. Cl.
CPC ................. *A61L 27/56* (2013.01); *A61F 2/28* (2013.01); *A61F 2/30* (2013.01); *A61L 27/24* (2013.01);
(Continued)

(58) Field of Classification Search
CPC ...... A61F 2002/2835; A61F 2002/2839; A61F 2002/30957; A61L 24/0036; A61L 27/56; A61L 2430/02; B29C 44/0469
See application file for complete search history.

(56) References Cited

U.S. PATENT DOCUMENTS 4,992,226 A       2/1991  Piez et al.
5,211,664 A   *   5/1993  Tepic ................... A61L 31/146
                                                  623/16.11
(Continued)

FOREIGN PATENT DOCUMENTS

CN          206683715 U      11/2017

OTHER PUBLICATIONS

International Search Report and Written Opinion dated Jan. 28, 2022.

*Primary Examiner* — Javier G Blanco
(74) *Attorney, Agent, or Firm* — Kevin M. Bull

(57) ABSTRACT

Disclosed are medical articles and processes for forming the medical articles. The medical articles may take the form of a sponge having a three-dimensional shape comprising a reservoir. In an embodiment, the sponge is formed by placing a collagen slurry, optionally further comprising a mineral, in a mold and lyophilizing the slurry. In an embodiment, an improved molding process for such medical articles comprises forcing a slurry through a mold comprising the shape of a tube having an obstruction connected to the sidewall of the tube via an arm extending from the sidewall to the obstruction.

19 Claims, 4 Drawing Sheets

(51) Int. Cl.
  *A61L 27/24*     (2006.01)
  *A61L 27/56*     (2006.01)
  *B29C 44/04*    (2006.01)

(52) U.S. Cl.
  CPC ................. *A61F 2002/2835* (2013.01); *A61F*
     *2002/30228* (2013.01); *A61F 2002/30957*
      (2013.01); *B29C 44/0469* (2013.01)

(56)       References Cited

U.S. PATENT DOCUMENTS

| | | | |
|---|---|---|---|
| 5,734,959 A * | 3/1998 | Krebs | ..................... A61L 27/30 |
| | | | 419/36 |
| 6,696,073 B2 | 2/2004 | Boyce et al. | |
| 7,824,703 B2 | 11/2010 | Scifert et al. | |
| 8,506,646 B2 * | 8/2013 | Mckay | ................... A61L 27/46 |
| | | | 623/23.61 |
| 9,220,596 B2 | 12/2015 | Cook et al. | |
| 9,931,435 B2 | 4/2018 | Scifert et al. | |
| 9,981,061 B2 | 5/2018 | Evans et al. | |
| 10,709,814 B2 | 7/2020 | Vickers et al. | |
| 2011/0012280 A1 * | 1/2011 | Deslauriers | ......... B29C 44/1214 |
| | | | 264/45.7 |
| 2011/0140316 A1 | 6/2011 | Bagga et al. | |

* cited by examiner

TISSUE REPAIR DEVICE AND MOLDING PROCESS

CROSS-REFERENCE TO RELATED APPLICATIONS

This application is a U.S. national phase entry under 35 USC § 371 of International Application No. PCT/US2021/057303, filed 29 Oct. 2021, which claims priority to U.S. Provisional Patent Application No. 63/107,618 filed on Oct. 30, 2020, U.S. Design application Ser. No. 29/756,896 filed on Oct. 30, 2020, and European Patent Application No. EP20209383.7 filed Nov. 24, 2020, the entire contents of each of which is expressly incorporated herein by reference.

FIELD

The disclosed inventions pertain to medical articles and molding processes therefor. The medical articles may be useful as devices for repairing tissue defects.

BACKGROUND

Medical articles for repairing tissue defects come in various forms and have various uses. One such medical article is a bone void filler in the form of a three-dimensional sponge. The sponge is typically in the form of a lyophilized composition of natural polymer(s). The sponge may be rehydrated, which makes it pliable. The rehydrating fluid may take various forms. Examples of the rehydrating fluid are sterile water, whole blood, platelet rich plasma (PRP), and bone marrow aspirate. Once made pliable, the material may be placed into a bone defect directly by hand or placed into a syringe and dispensed into a bone defect.

Such sponges are typically formed by first forming a slurry comprising water and particles or fibers of a biocompatible polymer. The slurry may further comprise a mineral, such as a mineral known to promote bone growth. Examples of such minerals are hydroxyapatite, calcium phosphates, bioactive glasses, bone particles, and mixtures thereof. The slurry is dispensed into a mold. The mold and slurry together are then placed in a freeze-dryer and the slurry lyophilized, resulting in a sponge. The sponge is then separated from the mold. Post-processing, such as machining to ensure suitable surface smoothness, may be carried out prior to packaging and sterilization.

An advancement in medical articles for treating tissue defects over the years has been improving the ease of use. One such advancement is to provide the medical article in a form that allows the treating doctor to easily rehydrate the medical article. One such commercially available product is MASTERGRAFT® Putty by Medtronic®. The product is a dish-shaped sponge made of a lyophilized composition of approximately 80 wt % mineral and 20 wt % of Type I bovine collagen. The mineral is in the form of particles present throughout the sponge. The mineral particles comprise approximately 15 wt % of hydroxyapatite and 85 wt % of β-tricalcium phosphate, based on the total weight of the particles.

The MASTERGRAFT® Putty sponge is in the form of a dish, having a reservoir that may hold the rehydrating fluid. The reservoir is formed by a perimeter sidewall and a recessed surface. The article has a rectangular cross-section. To use the material, the doctor dispenses the prescribed amount of rehydrating fluid directly into the dish. This has the advantage that the correct amount of rehydrating fluid is used and that the rehydrating fluid does not run off the sponge onto other surfaces. The doctor then manipulates the material to uniformly rehydrate the sponge with the rehydrating fluid, either manually or with the aid of tools. The rehydrated material is then placed into a tissue defect, either manually or with the aid of a syringe.

Further such medical articles are disclosed in U.S. Pat. No. 7,824,703. This publication described medically useful articles comprising a three-dimensional body including one or more implantable substances, wherein the body defines one or more reservoirs for receiving amounts of a biocompatible wetting liquid. In certain embodiments the body is disruptable upon wetting with the biocompatible liquid to form a conformable implantable material such as a putty, paste or more flowable wetted implant material.

Although sponges containing reservoirs or similar geometry may be desirable, they are not easily manufactured at scale.

SUMMARY

Air bubbles, fissures, and other imperfections often occur when lyophilizing such slurries in the mold. Air bubbles and imperfections are typically found at the mold/slurry interface because air bubbles formed at the interface cannot be removed easily. This is most prevalent at the bottom of the mold. These defects result in scrapped parts or additional time spent on post-processing. These defects are exacerbated when forming sponges having shapes comprising reservoirs as such shapes require additional mold surfaces in order to form the sidewall and recessed surface that define the reservoir.

It is possible to degas the molded slurry by vacuum, but this has the potential to distort the molded part as bubbles are pulled out of the molded slurry. Degassing via vacuum may also create unintended pores as gas is expanded within the slurry due to the decrease in pressure. This is particularly problematic as lyophilized sponges rely on liquid (typically water) to act as a porogen. Gas bubble porogens distort the pores created by liquid. Degassing is also inefficient as it adds an additional process step to the manufacturing process.

These difficulties may be overcome by applying the inventive processes and forming the inventive medical articles described herein.

In an embodiment, a medical article comprises a sponge in the form of a three-dimensional shape. The three-dimensional shape comprises a reservoir capable of holding a liquid, the reservoir defined by a sidewall and a recessed surface, wherein the sidewall comprises a plurality of cutouts extending from its top surface toward the recessed surface, wherein the plurality of cutouts extend through the width of the sidewall.

The cutouts may be formed as a result of the molding process described herein. In an embodiment, a method of forming a medical article comprising a sponge comprises the steps of:

a. providing a mold comprising
   i. a tube comprising a first open end, a second open end, and a wall extending therebetween, and
   ii. an obstruction present in the tube, wherein the obstruction is connected to the wall via an arm extending from the wall to the obstruction,
b. providing a slurry,
c. forcing the slurry through the tube from the first open end to the second open end and past the obstruction, thereby substantially filling the mold with slurry, and d. lyophilizing the slurry present in the mold, thereby forming a sponge.

Various benefits may be obtained by applying the inventive processes and forming the inventive medical articles described herein, including fewer part defects, lower scrap rates, increased manufacturing throughput, lower manufacturing costs, reduced post-processing time, greater flexibility of material composition and mineral loading in the slurry, improved mechanical properties of the medical articles, more consistency in final handling properties after rehydration, a lower likelihood of leaking fluids, and the ability to mold new geometries.

BRIEF DESCRIPTION OF THE DRAWINGS

FIG. 1 depicts a top perspective view of a medical article according to an embodiment of the invention.

FIG. 2 depicts a bottom perspective view of the medical article depicted in FIG. 1.

DETAILED DESCRIPTION

Figure 3:
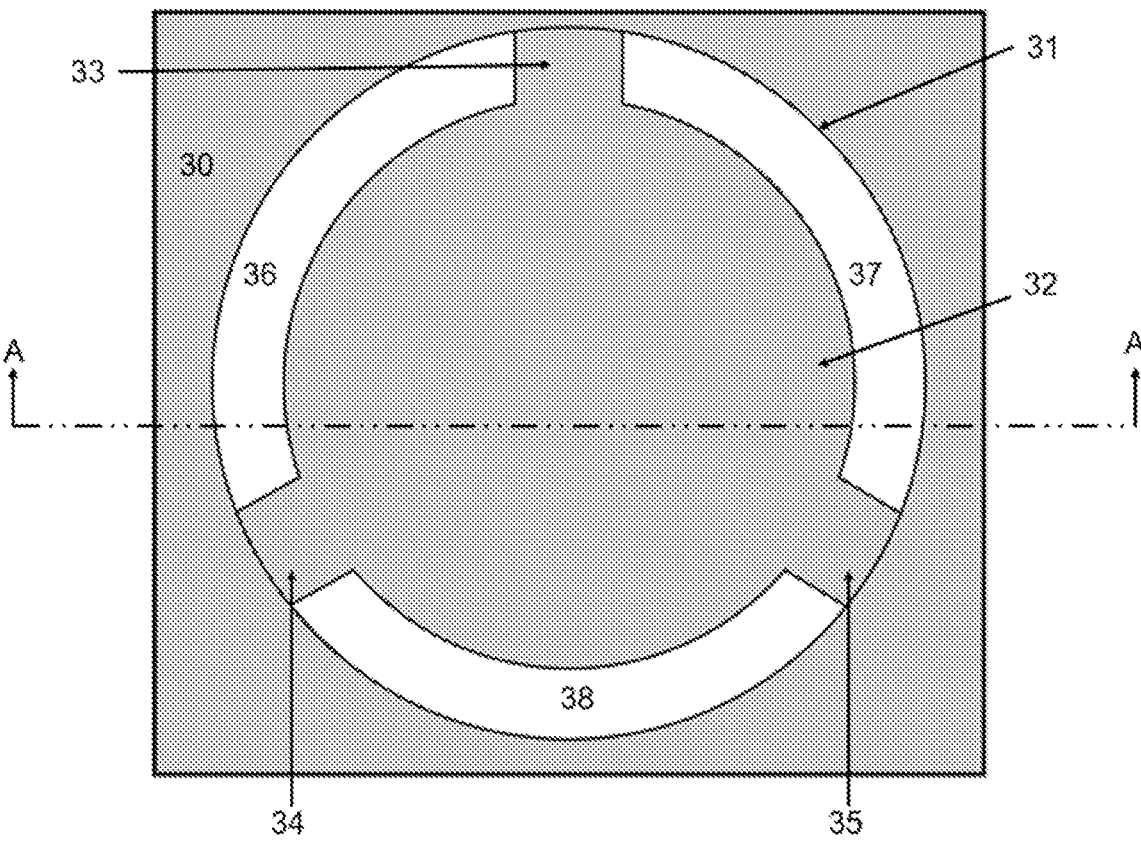
FIG. 3 depicts a top view of a mold that may be used with processes according to embodiments of the invention.

The medical articles described herein comprise a sponge in the form of a three-dimensional shape. The three-dimensional shape comprises a reservoir for holding a liquid. The liquid is generally a rehydrating fluid for the sponge. For example, the rehydrating fluid may be a sterile fluid, whole blood, a constituent of blood such as platelet rich plasma, or bone marrow aspirate.

The sponge may be formed by filling a mold with a slurry and lyophilizing the slurry in the mold, as described herein. In an embodiment, the slurry comprises water and fibers. In an embodiment, the fibers are polymer fibers. In an embodiment, the polymer fibers are fibers of a natural polymer. In an embodiment, the polymer fibers are fibers of a natural or synthetic biopolymer. In an embodiment, the slurry comprises soluble biopolymer of natural or synthetic origin. Examples of polymer fibers are fibers of collagen, chitosan, alginate, or hyaluronic acid. The fibers are preferably hydrophilic.

In an embodiment, the slurry or medical article comprises polymer fibers. In an embodiment, the medical article or slurry comprises collagen fibers. Collagen fibers are fibers of collagen and are insoluble in an aqueous liquid having a pH of 3.5. In an embodiment, the collagen fibers are native collagen fibers, as opposed to reconstituted collagen fibers. In an embodiment, the polymer fibers have an average length of from 1 to 15 mm. In an embodiment, the polymer fibers have an average length of from 0.5 mm to 10 mm. In an embodiment, the polymer fibers have an average length of at least 0.5 mm, at least 1 mm, at least 2 mm, at least 3 mm, or at least 4 mm. In an embodiment, the polymer fibers have an average length of at most 15 mm, at most 12 mm, at most 10 mm, at most 9 mm, at most 8 mm, at most 7 mm, at most 6 mm, at most 5 mm, or at most 4 mm.

Native collagen fibers may have fiber lengths of 50 mm or more. Collagen fiber length may be controlled by known processing methods. For example, average fiber length may be controlled by centrifugal milling of collagen fibers using a cutting head of a suitable gap size. A cutting head gap size of 5 mm yields an average fiber length of 5 mm. If centrifugal mill cutting head gap size is not known or is substantially non-uniform, average fiber length may be measured using optical comparators or light microscopes.

In an embodiment, the sponge or medical article further comprises acid-soluble collagen. Acid-soluble collagen is collagen that is in a form that is insoluble in an aqueous liquid having a pH of 6.5 and is soluble in an aqueous liquid having a pH of 4. To solubilize the collagen in solution, the pH is driven down to from 2 to 4. However, once in solution, the pH can be brought up to 6.5 without coming out of solution. The acid-soluble collagen is introduced into liquid as particles or a powder in order to form the slurry.

In an embodiment, the acid-soluble collagen has been processed without the aid of enzymes and is thus non-enzymatically processed, acid-soluble collagen. Non-enzymatically processed, acid-soluble collagen may be produced by milling a cleaned collagen source material, such as hides or skins. Typically, collagen for use in the invention can be obtained from any suitable animal source, for example, bovine, porcine, piscine, ovine, caprine, or other sources. The tropocollagen resulting from non-enzymatic processing is unable to undergo spontaneous fibrillation under physiological conditions.

In an embodiment, the ratio of collagen fibers to acid-soluble collagen by weight in the sponge or slurry is from 25:75 to 75:25. In an embodiment, the dry sponge or slurry comprises from 10 to 75 wt % of acid-soluble collagen and from 25 to 90 wt % of collagen fibers, based on the total amount of collagen in the dry sponge or slurry, respectively.

In an embodiment, the slurry or medical article further comprises a mineral. The mineral may be present as particles or fibers. Upon lyophilizing the slurry, the mineral is supported by and retained in the network of polymer fibers. In an embodiment, the mineral is present as particles with an average particle diameter of from 0.05 to 5 mm. In an embodiment, the mineral is present as particles having an average particle diameter of at least 0.05, at least 0.1, at least 0.2, at least 0.3, at least 0.4, or at least 0.5 mm. In an embodiment, the mineral is present as particles having an average particle diameter of at most 5, at most 4, at most 3, at most 2, at least 1, or at least 0.5 mm.

In an embodiment, the slurry is highly resistant to flow. In an embodiment, the slurry may be placed at room temperature into a cylinder having two open ends and the filled cylinder turned on its wall such that the longitudinal axis of the cylinder faces horizontally, and there will be no substantial leakage of the slurry for at least 30 seconds. In an embodiment, the slurry may be placed at room temperature into a cylinder having two open ends and the filled cylinder turned on its wall such that the longitudinal axis of the cylinder faces horizontally, and there will be no substantial leakage of the slurry for at least 30 seconds, at least 1 minute, at least 5 minutes, at least 10 minutes, at least 15 minutes, at least 30 minutes, or at least 1 hour. In an embodiment, the mineral comprises hydroxyapatite, bioactive glass, a tricalcium phosphate such as α-tricalcium phosphate or β-tricalcium phosphate, or a bone particle. The bone particle may be anorganic bone particles, autologous bone particles, allogenic bone particles, or xenogenic bone particles, or a combination thereof. The mineral may be monophasic or biphasic. In an embodiment, the dry sponge or slurry comprises from 65, 66, 67, 68, 69, 70, 71, 72, 73, 74, 75, 76, 77, 78, 79, or 80 wt % to 95, 94, 93, 92, 91, 90, 89, 88, 87, 86, or 85 wt % of mineral, based on the total weight of the dry sponge or the solids of the slurry, respectively. In an embodiment, the dry sponge or slurry comprises collagen and a mineral, wherein the collagen is present from 5, 6, 7, 8, 9, 10, 11, 12, 13, 14, or 15 wt % to 30, 29, 28, 27, 26, 25, 24, 23, 22, 21, 20, 19, 18, 17, or 16 wt %, based on the total weight of the dry sponge or the solids of the slurry, respectively.

The medical article may be formed by first forming a slurry. In an embodiment, the slurry comprises water and polymer fibers. In an embodiment, the slurry further comprises other components, such as acid-soluble collagen or a mineral. The working pH range for a slurry containing collagen fibers and/or acid-soluble collagen is typically from 2 to 8. In an embodiment, the pH of the slurry is from 4.5 to 8. In an embodiment, the slurry further comprises an acid, a base, or a buffer. Generally, the acid or base is added to the slurry to bring the slurry to the desired pH. In the case of a collagen-containing slurry, the viscosity of the slurry is dependent on such factors as the pH of the slurry, the fiber length of collagen fibers, the ratio of fibrous collagen to soluble collagen, and the solids content of the slurry.

In an embodiment, the slurry has a solids content of from 2 to 30 wt %, based on the total weight of the slurry. Solids content is what is left after removing the liquid components of the slurry, for instance after lyophilizing the slurry. In an embodiment, the slurry has a solids content of at least 2, 5, or 10 wt %, based on the total weight of the slurry. In an embodiment, the slurry has a solids content of at most 40, 35, 30, 25, 20, 15, or 10 wt %, based on the total weight of the slurry. The solids content by weight of the slurry will generally be higher when a mineral is present in the slurry than when a mineral is not present in the slurry. In an embodiment, the slurry does not comprise a mineral and the slurry has a solids content of from 2 to 10 wt %. In an embodiment, the slurry comprises a mineral and the slurry has a solids content of from 10 to 40 wt %.

In an embodiment, the slurry is introduced into a mold and lyophilized, thereby forming a sponge. This method of forming a sponge generally leads to a sponge having randomly aligned fibers. Following lyophilization, the sponge may be cross-linked. In an embodiment, cross-linking is performed without use of chemicals, such as by dehydrothermally cross-linking a collagen sponge. In an embodiment, cross-linking is performed with the use of chemicals, such as glutaraldehyde. The final device may be obtained by cutting the material after cross-linking, such as with a laser or mill.

In an embodiment, the medical article has a footprint that is circular, elliptical, or polygonal. In an embodiment, the medical article is in the general shape of a cylinder, elliptical cylinder, or polyhedron.

In an embodiment, the medical article comprises at least one reservoir. In an embodiment, the reservoir is defined by a recessed surface and a sidewall. The recessed surface may be flat or curved. The recessed surface is typically positioned opposite the base surface. In an embodiment, the sidewall is a perimeter sidewall, running along the perimeter of the medical article. In an embodiment, the sidewall is formed by a top surface, an inner sidewall surface, and an outer sidewall surface.

In an embodiment, the medical article comprises a sidewall comprising a cutout. In an embodiment, at least one cutout results from the molding process for forming the medical article. Other cutouts may also result from the molding process or may be added during post-processing. The cutouts can have various shapes, such as cross-sections of squares, rectangles, trapezoids, portions of circles, or portions of ellipses. The cutouts generally begin at the top surface of the sidewall, extend through the entire sidewall, but do not reach the recessed surface. This is so that rehydrating fluid may be retained in the recessed surface bordered by the sidewall without spilling through the cutouts. The cutouts may serve as an indicator for the proper amount of rehydrating fluid that should be deposited in the reservoir to suitably rehydrate the medical article.

Figure 1:
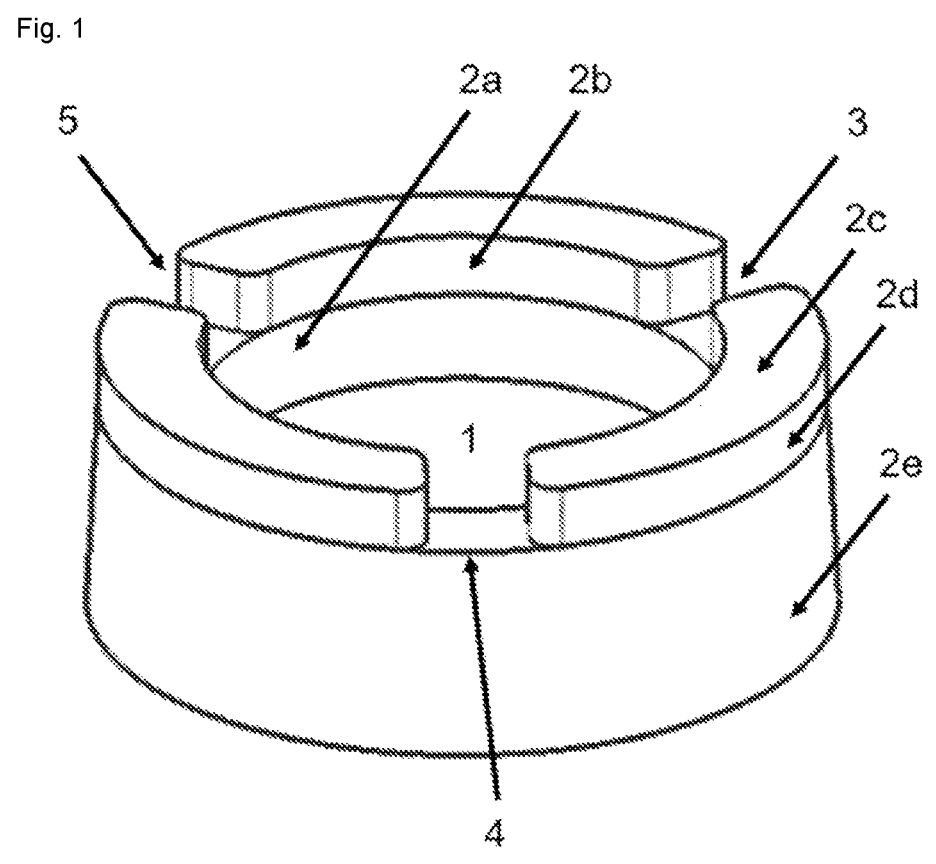
Figure 2:
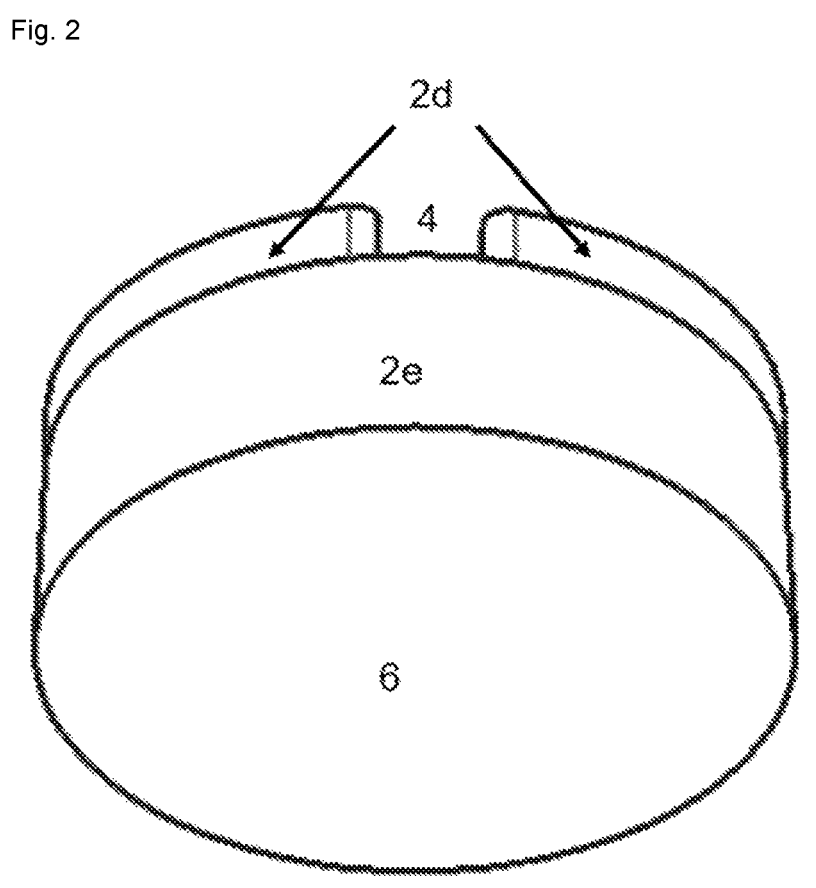

A medical article according to an embodiment of the invention is shown in FIG. 1 and FIG. 2. The medical article comprises a sponge comprising a reservoir. The reservoir is formed by recessed surface 1 and a sidewall. The sidewall is composed of multiple surfaces, 2a, 2b, 2c, 2d, the portion of surface 2e that extends above recessed surface 1, and along with the surfaces forming cutouts 3, 4, and 5. The outer sidewall is broken into two sections, surface 2d and the portion of surface 2e that extends above recessed surface 1.

Recessed surface 1 is substantially planar. In an embodiment, recessed surface 1 is concave. Bottom surface 6 is substantially planar. The inner sidewall is composed of multiple surfaces 2a and 2b. Lower inner sidewall surface 2a meets recessed surface 1 at an angle of approximately 93 degrees. Upper inner sidewall surface 2b meets lower inner sidewall surface 2a at an angle of approximately 177 degrees, such that upper inner sidewall surface 2b and recessed surface 1 are substantially perpendicular. Upper inner sidewall surface 2b is broken into three sections by cutouts 3, 4, and 5. Lower inner sidewall surface 2a and upper inner sidewall surface 2b together form an inner sidewall surface.

Recessed surface 1 is present opposite bottom surface 6. Bottom surface 6 forms the base of the medical article. Lower outer surface 2e meets bottom surface 6 at an angle of approximately 87 degrees. Upper outer surface 2d extends from lower outer surface 2e at an angle of 177 degrees, such that upper outer surface 2d and bottom surface 6 are substantially perpendicular. Upper outer surface 2d is substantially perpendicular to top surface 2c. Lower outer surface 2e and upper outer surface 2d together form an outer surface. The upper outer surface 2d and the portion of lower outer surface 2e that extends above recessed surface 1 together form an outer sidewall surface.

In an embodiment, the outer surface comprises a first surface and a second surface, wherein the surfaces meet at an angle of less than 180 degrees. In an embodiment, the outer surface comprises a first surface and a second surface, wherein the surfaces meet at an angle of from 160 to 179 degrees.

In an embodiment, the inner sidewall surface comprises a first surface and a second surface, wherein the surfaces meet at an angle of less than 180 degrees. In an embodiment, the inner sidewall surface comprises a first surface and a second surface, wherein the surfaces meet at an angle of from 160 to 179 degrees.

In an embodiment, the sidewall comprises a surface that meets the recessed surface at an angle of greater than 90 degrees. In an embodiment, the sidewall comprises a surface that meets the recessed surface at an angle of from 91 to 110 degrees. In an embodiment, the outer surface comprises a surface that meets the bottom surface at an angle of from 70 to 89 degrees.

Top surface 2c, upper inner sidewall surface 2b, and upper outer surface 2d are broken into multiple sections by cutouts 3, 4, and 5. The cutouts are formed as a result of the molding process described herein. As depicted, the edges of the cutouts are rounded at the intersection of the cutouts with upper outer surface 2d and upper inner sidewall surface 2b. Otherwise, the angles formed are approximately 90 degrees for ease of post-process machining.

As depicted in FIG. 1 and FIG. 2, the portion of the sidewall between the bottom and the cutouts may be angled differently than the rest of the medical article in order to facilitate post-processing. For example, this portion of the device may comprise surfaces that intersect at approximately 90 degrees.

Figure 4:
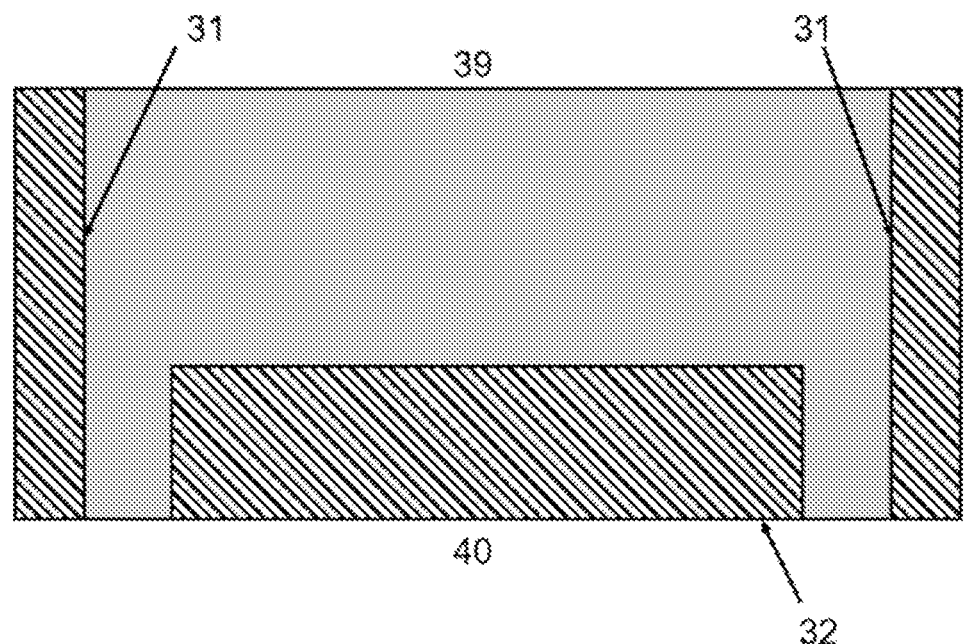
FIG. 4 depicts a cross-section of the mold depicted in FIG. 3.

FIG. 3 and FIG. 4. depict a top view, and a cross-section, respectively, of a mold suitable for forming a medical article shaped similarly to the medical article depicted in FIG. 1 and FIG. 2. The main difference between the medical article pictured in FIG. 1 and FIG. 2 and the molds depicted in FIG. 3 and FIG. 4 is that the depicted mold is not capable of forming surfaces that meet at angles of less than or greater than 90 degrees. Rather, the molds in FIG. 3 and FIG. 4 are depicted such that all surfaces meet at 90 degree angles and no corners are rounded for simplicity. Although corners are shown as not rounded, the resulting medical articles may still have a slight radius resulting from the mold machining process.

As depicted in FIG. 3, mold 30 comprises a circular wall 31 with a circular obstruction 32 present within it over less than the full height of the mold. Obstruction 32 is supported within the mold by arms 33, 34, 35 connecting obstruction 32 with wall 31. The obstruction and the arms together thus define open spaces 36, 37, and 38, which allows slurry to pass on the sides of obstruction 31 and arms 33, 34, 35. The molds are typically present in a block-shaped tray containing numerous molds as depicted in FIG. 3 and FIG. 4.

FIG. 4 depicts cross-section A-A of the mold shown in FIG. 3. Obstruction 32 and arms (not pictured) are present over less than the full height of the mold. The mold comprises a tube having a circular inner surface 31. The interior of the tube thus generally comprises a shape of a cylinder having a fully open end 39 and partially obstructed end 40. Slurry may be deposited in end 39 to fill the mold. The recessed surface of the medical article is formed against the top surface of obstruction 32. The cutouts are formed around arms 33, 34, 35. The top surface of the sidewall is formed at partially obstructed end 40.

Typically, the mold is overfilled with slurry, causing excess slurry to be present on either end 39, 40 of the mold. Excess slurry is scraped off. Thereafter, the mold is placed on a tray, typically with partially obstructed end 40 facing the tray, and the mold and tray together placed in the freeze-dryer.

Figure 5:
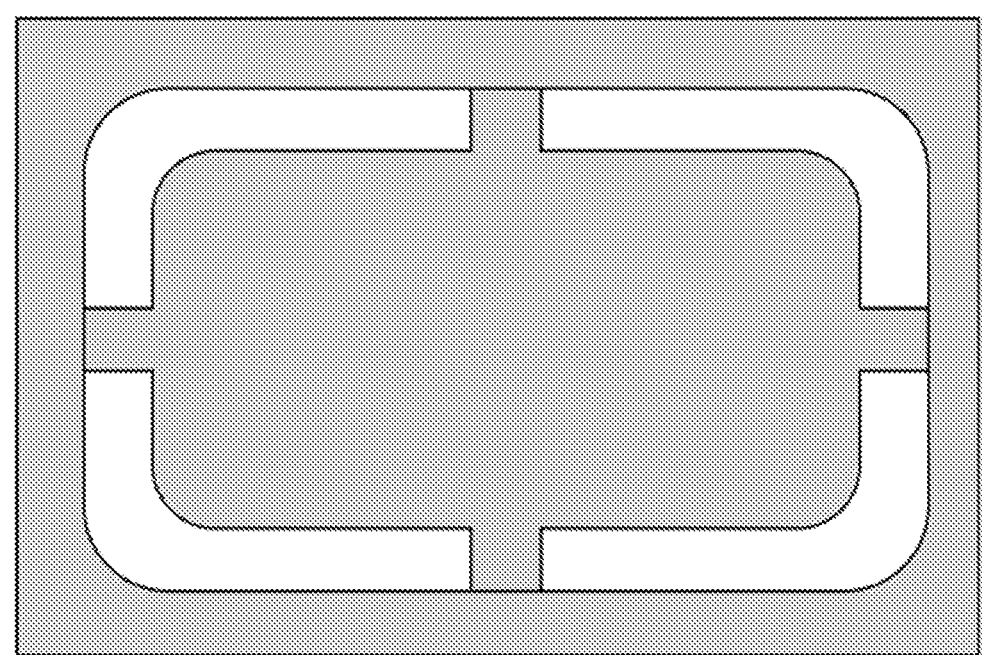
FIG. 5 depicts a top view of a mold that may be used with processes according to embodiments of the invention.

FIG. 5 depicts a further embodiment of a mold. The mold depicted in FIG. 5 may be suitable for forming a medical article comprising a substantially rectangular footprint with four cutouts in its sidewall.

In an embodiment, the medical article further comprises a bioactive agent. The bioactive agent may be, for example, a steroid, an anti-inflammatory agent, an antibiotic, or another bioactive agent that may be useful to treat a wound or inflammation. The bioactive agent may be present in the interior of the sponge, such as by soaking the sponge in the bioactive agent or by mixing in microparticles comprising the bioactive agent when forming the sponge. The bioactive agent may also be present on an exterior surface by forming a coating on the exterior of the sponge. The coating may be formed by, for example, dissolving a bioactive agent in a degradable synthetic polymer and coating the solution on an exterior surface of the sponge. Suitable degradable synthetic polymers may comprise a polylactic acid (PLA), polyglycolic acid (PGA), poly(lactic-co-glycolic acid) (PLGA), polycaprolactone (PCL), polyester amide (PEA) or a combinations thereof or a co-polymer thereof.

In an embodiment, the medical article is a tissue repair device. In an embodiment, the tissue repair device is a bone void filler or suitable for use in filling a defect in bone.

EXAMPLES

An aqueous slurry was prepared comprising native, insoluble collagen fibers (Semed F, DSM Biomedical) and acid-soluble collagen (Semed S, DSM Biomedical) at 4.2% solids by weight. The aqueous slurry is then combined with a mineral having a particle size of about 90-600 μm to yield a combined mixture of 83 wt % mineral and 17 wt % collagen, based on the total weight of the mineral and collagen in the mixture. The mixture is then freeze-dried in one of two different mold types as follows.

A first mold (referred to hereafter as the "open mold") has a circular cross-section and comprises two open ends and an obstruction, similar to the mold depicted in FIG. 3. The obstruction is connected to the walls of the tube via six arms. This mold results in parts similar in geometry to those depicted in FIG. 1, but with six cutouts instead of three. The overall mold dimensions are 60 mm in diameter and 11 mm in height.

A second mold (referred to hereafter as the "closed mold") has a rectangular cross-section with rounded edges. The mold is similar to as depicted in FIG. 5 but is closed on the end comprising the obstructions such that no arms are present and the slurry cannot flow through the mold. The resulting shape has no cutouts present in the sidewall. The mold dimensions are approximately 67 mm in length, 47 mm in width, and 8.3 mm in height.

Three samples for each of the open mold and the closed mold are formed as follows. The mold cavity is filled with mixture and the excess mixture removed. The mold is then placed on a tray and lyophilized. After lyophilization, the samples were separated from the molds and analyzed visually by comparing the number of air bubbles found in the surfaces of each sample. Results are shown in Table 1.

TABLE 1

| | Number of Air Bubbles | |
| --- | --- | --- |
| | Open Mold (# of Air Bubbles) | Closed Mold (# of Air Bubbles) |
| Sample 1 | 1 | 4 |
| Sample 2 | 0 | 5 |
| Sample 3 | 1 | 9 |
| Average | 0.67 | 6 |

Significantly fewer air bubbles were detected when molding using the open mold than the closed mold. In addition, samples molded using the open mold had a smoother bottom surface while the closed mold samples have an uneven bottom surface.

Additional Description of Exemplary Embodiments

1. A medical article comprising a sponge in the form of a three-dimensional shape, the three-dimensional shape comprising a reservoir capable of holding a liquid, the reservoir defined by a sidewall and a recessed surface, wherein the sidewall comprises a plurality of cutouts extending from its top surface toward the recessed surface, wherein the plurality of cutouts extend through the width of the sidewall.

2. A medical article comprising a sponge in the form of a three-dimensional shape comprising: a base surface, a top surface, a recessed surface opposite the base surface, an outer surface extending between the base surface and the top surface, and an inner sidewall surface extending between the recessed surface and the top surface, wherein the three-dimensional shape comprises a plurality of cutouts extending from the top surface and through the inner sidewall surface and the outer surface.

3. A method of forming a medical article, the method comprising the steps of:
    a. providing a mold comprising:
        i. a tube comprising a first open end, a second open end, and a wall extending therebetween, and
        ii. an obstruction present in the tube,
    b. providing a slurry comprising water and fibers,
    c. forcing the slurry through the tube from the first open end to the second open end and past the obstruction, thereby substantially filling the mold with slurry, and
    d. lyophilizing the slurry present in the mold, thereby forming a medical article comprising a reservoir.

4. A method of forming a medical article comprising a sponge, the method comprising the steps of:
    a. providing a mold comprising
        i. a tube comprising a first open end, a second open end, and a wall extending therebetween, and
        ii. an obstruction present in the tube, wherein the obstruction is connected to the wall via an arm extending from the wall to the obstruction,
    b. providing a slurry comprising water,
    c. forcing the slurry through the tube from the first open end to the second open end and past the obstruction, thereby substantially filling the mold with slurry, and
    d. lyophilizing the slurry present in the mold, thereby forming a sponge.

5. The medical article or method according to any one of the previous exemplary embodiments, wherein the sponge or slurry comprises polymer fibers.

6. The medical article or method according to any one of the previous exemplary embodiments, wherein the sponge or slurry comprises a biopolymer.

7. The medical article or method according to any one of the previous exemplary embodiments, wherein the sponge or slurry comprises soluble biopolymer of natural or synthetic origin.

8. The method according to any one of the previous exemplary embodiments, further comprising the step of separating the sponge from the mold.

9. The method according to any one of the previous exemplary embodiments, further comprising the step of separating slurry that has been not advanced through the mold past the first open end prior to lyophilizing.

10. The method according to any one of the previous exemplary embodiments, further comprising the step of separating slurry that has been advanced through the mold past the second open end prior to lyophilizing.

11. The method according to any one of the previous exemplary embodiments, wherein the sponge comprises a reservoir and a sidewall comprising a cutout.

12. The method according to any one of the previous exemplary embodiments, wherein the sponge comprises a reservoir formed from a sidewall and a recessed surface, and wherein the sidewall comprises a cutout.

13. The method according to any one of the previous exemplary embodiments, further comprising the step of cross-linking the sponge.

14. The method according to any one of the previous exemplary embodiments, wherein the slurry comprises water and polymer fibers.

15. The medical article or method according to any one of the previous exemplary embodiments, wherein the sponge is a based on a natural polymer.

16. The medical article or method according to any one of the previous exemplary embodiments, wherein the sponge is a collagen-based sponge.

17. The medical article or method according to any one of the previous exemplary embodiments, wherein the slurry or sponge comprises fibers of a natural polymer.

18. The medical article or method according to any one of the previous exemplary embodiments, wherein the slurry or sponge comprises fibers of a natural or synthetic biopolymer.

19. The medical article or method according to any one of the previous exemplary embodiments, wherein the slurry or sponge further comprises acid-soluble collagen 20. The medical article or method according to any one of the previous exemplary embodiments, wherein the slurry or sponge comprises acid-soluble collagen and collagen fibers.

21. The medical article or method according to any one of the previous exemplary embodiments, wherein the slurry or sponge further comprises a mineral.

22. The medical article or method according to any one of the previous exemplary embodiments, wherein the sponge further comprises a mineral and the mineral is present as particles having an average particle diameter of from 0.05 to 5 mm, or from 0.05 to 2 mm.

23. The medical article or method according to any one of the previous exemplary embodiments, wherein the mineral is present as particles having an average particle diameter of at least 0.05, at least 0.1, at least 0.2, at least 0.3, at least 0.4, or at least 0.5 mm.

24. The medical article or method according to any one of the previous exemplary embodiments, wherein the mineral is present as particles having an average particle diameter of at most 5, at most 4, at most 3, at most 2, at least 1, or at least 0.5 mm.

25. The medical article or method according to any one of the previous exemplary embodiments, wherein the dry sponge or slurry comprises from 50 to 95 wt % of mineral and from 5 to 50 wt % of collagen, based on the total weight of the dry sponge or the solids of the slurry, respectively.

26. The medical article or method according to any one of the previous exemplary embodiments, wherein the dry sponge or slurry comprises from 5, 6, 7, 8, 9, 10, 11, 12, 13, 14, or 15 wt % to 30, 29, 28, 27, 26, 25, 24, 23, 22, 21, 20, 19, 18, 17, or 16 wt % of collagen, based on the total weight of the dry sponge or the solids of the slurry, respectively.

27. The medical article or method according to any one of the previous exemplary embodiments, wherein the dry sponge or slurry comprises from 65, 66, 67, 68, 69, 70, 71, 72, 73, 74, 75, 76, 77, 78, 79, or 80 wt % to 95, 94, 93, 92, 91, 90, 89, 88, 87, 86, or 85 wt % of mineral, based on the total weight of the dry sponge or the solids of the slurry, respectively.

28. The medical article or method according to any one of the previous exemplary embodiments, wherein the dry sponge or slurry comprises from 10 to 75 wt % of acid-soluble collagen and from 25 to 90 wt % of collagen fibers, based on the total amount of collagen in the dry sponge or slurry, respectively.

29. The medical article or method according to any one of the previous exemplary embodiments, wherein the ratio of collagen fibers to acid-soluble collagen by weight in the sponge or slurry is from 25:75 to 75:25.

30. The medical article or method according to any one of the previous exemplary embodiments, wherein the sponge is cross-linked.

31. The medical article or method according to any one of the previous exemplary embodiments, wherein the sponge is formed by lyophilizing a slurry comprising collagen and water.

32. The medical article or method according to any one of the previous exemplary embodiments, wherein the sponge is formed by lyophilizing a slurry comprising acid-soluble collagen, collagen fibers, and water.

33. The medical article or method according to any one of the previous exemplary embodiments, wherein the sponge is formed by lyophilizing a slurry comprising acid-soluble collagen, collagen fibers, mineral particles, and water.

34. The medical article or method according to any one of the previous exemplary embodiments, wherein the slurry has a pH of from 4.5 to 8.

35. The medical article or method according to any one of the previous exemplary embodiments, wherein the slurry further comprises an acid, a base, or a buffer.

36. The medical article or method according to any one of the previous exemplary embodiments, wherein the slurry has a solids content of from 2 to 30 wt %, based on the total weight of the slurry.

37. The medical article or method according to any one of the previous exemplary embodiments, wherein the slurry has a solids content of at least 2, 5, or 10 wt %, based on the total weight of the slurry.

38. The medical article or method according to any one of the previous exemplary embodiments, wherein the slurry has a solids content of at most 40, 35, 30, 25, 20, 15, or wt %, based on the total weight of the slurry.

39. The medical article or method according to any one of the previous exemplary embodiments, wherein the slurry does not comprise a mineral and the slurry has a solids content of from 2 to 10 wt %.

40. The medical article or method according to any one of the previous exemplary embodiments, wherein the slurry comprises a mineral and the slurry has a solids content of from 10 to 40 wt %.

41. The medical article or method according to any one of the previous exemplary embodiments, wherein the slurry may be placed at room temperature into a cylinder having two open ends and the filled cylinder turned on its wall such that the longitudinal axis of the cylinder faces horizontally, and there will be no substantial leakage of the slurry for at least seconds, at least 1 minute, at least 5 minutes, at least 10 minutes, at least 15 minutes, at least 30 minutes, or at least 1 hour.

42. The medical article or method according to any one of the previous exemplary embodiments, wherein the acid-soluble collagen is processed without the use of enzymes.

43. The medical article or method according to any one of the previous exemplary embodiments, wherein the collagen fibers are native collagen fibers.

44. The medical article or method according to any one of the previous exemplary embodiments, wherein the polymer fibers have an average length of from 1 to 15 mm.

45. The medical article or method according to any one of the previous exemplary embodiments, wherein the polymer fibers have an average length of from 0.5 mm to 10 mm.

46. The medical article or method according to any one of the previous exemplary embodiments, wherein the polymer fibers have an average length of from 1 mm to 5 mm.

47. The medical article or method according to any one of the previous exemplary embodiments, wherein the polymer fibers have an average length of at least 0.5 mm, at least 1 mm, at least 2 mm, at least 3 mm, or at least 4 mm.

48. The medical article or method according to any one of the previous exemplary embodiments, wherein the polymer fibers have an average length of at most 15 mm, at most 12 mm, at most 10 mm, at most 9 mm, at most 8 mm, at most 7 mm, at most 6 mm, at most 5 mm, or at most 4 mm.

49. The method according to any one of the previous exemplary embodiments, further comprising the step of centrifugally milling native collagen fibers.

50. The medical article or method according to any one of the previous exemplary embodiments, further comprising the step of cutting the medical article into a desired shape.

51. The medical article or method according to any one of the previous exemplary embodiments, further comprising the step of laser cutting the collagen sponge into a desired shape.

52. The medical article or method according to any one of the previous exemplary embodiments, further comprising the step of milling a surface of the medical article into a desired shape.

53. The medical article or method according to any one of the previous exemplary embodiments, wherein the medical article has a footprint that is circular, elliptical, or polygonal.

54. The medical article or method according to any one of the previous exemplary embodiments, wherein the medical article is in the general shape of a cylinder, elliptical cylinder, or polyhedron.

55. The medical article or method according to any one of the previous exemplary embodiments, wherein the medical article is in the form of a three-dimensional shape, the three-dimensional shape comprising a reservoir capable of holding a liquid, the reservoir defined by a sidewall and a recessed surface, wherein the sidewall comprises a plurality of cutouts extending from its top surface toward the recessed surface, wherein the plurality of cutouts extend through the width of the sidewall.

56. The medical article or method according to any one of the previous exemplary embodiments, wherein the medical article is in the form of a three-dimensional shape comprising: a base surface, a top surface, a recessed surface opposite the base surface, an outer surface extending between the base surface and the top surface, and an inner sidewall surface extending between the recessed surface and the top surface, wherein the three-dimensional shape comprises a plurality of cutouts extending from the top surface and through the inner sidewall surface and the outer surface.

57. The medical article or method according to any one of the previous exemplary embodiments, wherein the bottom surface or base of the medical article is a planar surface.

58. The medical article or method according to any one of the previous exemplary embodiments, wherein the sidewall is a perimeter sidewall.

59. The medical article or method according to any one of the previous exemplary embodiments, wherein the sidewall is in the shape of an annulus.

60. The medical article or method according to any one of the previous exemplary embodiments, wherein the top surface is an annular surface.

61. The medical article or method according to any one of the previous exemplary embodiments, wherein the outer surface and the base or bottom surface of the medical article intersect at an angle of less than 90 degrees.

62. The medical article or method according to any one of the previous exemplary embodiments, wherein the outer surface and the base or bottom surface of the medical article intersect at an angle of from than 80 to 88 degrees.

63. The medical article or method according to any one of the previous exemplary embodiments, wherein the top surface of the sidewall meets the inner surface of the sidewall at an angle of approximately 90 degrees.

64. The medical article or method according to any one of the previous exemplary embodiments, wherein the top surface of the sidewall meets the outer surface of the sidewall at an angle of approximately 90 degrees.

65. The medical article or method according to any one of the previous exemplary embodiments, wherein the inner surface of the sidewall meets the recessed surface at an angle of approximately 90 degrees.

66. The medical article or method according to any one of the previous exemplary embodiments, wherein the inner surface of the sidewall meets the recessed surface at an angle of greater than 90 degrees.

67. The medical article or method according to any one of the previous exemplary embodiments, wherein the recessed surface is planar.

68. The medical article or method according to any one of the previous exemplary embodiments, wherein the recessed surface is curved.

69. The medical article or method according to any one of the previous exemplary embodiments, wherein the recessed surface is concave.

70. The medical article or method according to any one of the previous exemplary embodiments, wherein the recessed surface is parabolic.

71. The method according to any one of the previous exemplary embodiments, wherein the obstruction comprises a convex surface 72. The medical article or method according to any one of the previous exemplary embodiments, wherein the outer surface comprises a first portion and a second portion, the first portion extending at an angle of less than 90 degrees relative to the base or bottom surface, and a second portion extending at an angle of approximately 90 degrees relative to the base or bottom surface.

73. The medical article or method according to any one of the previous exemplary embodiments, wherein the outer surface comprises a first portion and a second portion, the first portion beginning from a first end at an angle of less than 90 degrees relative to the base or bottom surface, and a second portion ending at the top surface at an angle of approximately 90 degrees relative to the base or bottom surface.

74. The medical article or method according to any one of the previous exemplary embodiments, wherein the outer surface comprises a first surface and a second surface, wherein the surfaces meet at an angle of less than 180 degrees.

75. The medical article or method according to any one of the previous exemplary embodiments, wherein the outer surface comprises a first surface and a second surface, wherein the surfaces meet at an angle of from 160 to 179 degrees.

76. The medical article or method according to any one of the previous exemplary embodiments, wherein the inner sidewall surface comprises a first surface and a second surface, wherein the surfaces meet at an angle of less than 180 degrees.

77. The medical article or method according to any one of the previous exemplary embodiments, wherein the inner sidewall surface comprises a first surface and a second surface, wherein the surfaces meet at an angle of from 160 to 179 degrees.

78. The medical article or method according to any one of the previous exemplary embodiments, wherein the sidewall comprises a surface that meets the recessed surface at an angle of greater than 90 degrees.

79. The medical article or method according to any one of the previous exemplary embodiments, wherein the sidewall comprises a surface that meets the recessed surface at an angle of from 91 to 110 degrees.

80. The medical article or method according to any one of the previous exemplary embodiments, wherein the outer surface comprises a surface that meets the bottom surface at an angle of from 70 to 89 degrees.

81. The medical article or method according to any one of the previous exemplary embodiments, wherein the sidewall comprises a cutout.

82. The medical article or method according to any one of the previous exemplary embodiments, wherein the sidewall comprises two, three, four, five, six, seven, or eight cutouts.

83. The medical article or method according to any one of the previous exemplary embodiments, wherein the sidewall comprises from two to eight cutouts.

84. The medical article or method according to any one of the previous exemplary embodiments, wherein the cutout has the cross-sectional shape of a square, rectangle, trapezoid, portion of an ellipse, or portion of a circle.

85. The medical article or method according to any one of the previous exemplary embodiments, wherein the cutout has the shape of a cube, rectangular prism, trapezoidal prism, portion of a sphere, or portion of an ellipsoid.

86. The medical article or method according to any one of the previous exemplary embodiments, wherein the sidewall comprises a plurality of evenly spaced cutouts.

87. The medical article or method according to any one of the previous exemplary embodiments, wherein the sidewall comprises one or more cutouts composed of surfaces that intersect each other approximately 90 degrees.

88. The medical article or method according to any one of the previous exemplary embodiments, wherein the sidewall comprises a cutout that extends from the top surface of the sidewall in the direction of the recessed surface but does not reach the recessed surface.

89. The medical article or method according to any one of the previous exemplary embodiments, wherein the dimensions of the cutout indicate the height of rehydrating fluid that should be deposited in the reservoir in order to properly rehydrate the medical article.

90. The medical article or method according to any one of the previous exemplary embodiments, wherein the medical article has a volume of 0.5 to 15 cubic centimeters.

91. The medical article or method according to any one of the previous exemplary embodiments, wherein the medical article or slurry further comprises a bioactive agent.

92. The method or medical article according to any one of the previous exemplary embodiments, wherein the medical article or slurry further comprises bone morphogenetic protein, demineralized bone matrix, growth factor, or stem cells.

93. The medical article or method according to any one of the previous exemplary embodiments, further comprising a coating comprising a bioactive agent present on an exterior surface of the medical article.

94. A medical article formed according to the method of any one of the previous exemplary embodiments.

95. A medical article formed according to the method of any one of the previous exemplary embodiments, wherein the medical article comprises at least one reservoir.

96. A method of treating a bone defect comprising the steps of:

a. providing the medical article according to any one of the previous exemplary embodiments, b. placing a liquid in the reservoir, c. manipulating the medical article such that the liquid is absorbed into and rehydrates the medical article, thereby forming a putty, d. inserting the putty into a bone defect of a patient.

97. The method of treating a bone defect of the previous exemplary embodiment, further comprising the step of: placing the putty in a syringe, wherein the step of inserting the putty into a bone defect of a patient is performed by dispensing the putty into the bone defect via the syringe.

98. The medical article or method according to any one of the previous exemplary embodiments, wherein the medical article is a tissue repair device.

99. The medical article or method according to any one of the previous exemplary embodiments, wherein the medical article is a bone void filler or suitable for use in filling a defect in bone.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. While certain optional features are described as embodiments of the invention, the description is meant to encompass and specifically disclose all combinations of these embodiments unless specifically indicated otherwise or physically impossible.

The invention claimed is:

1. A method of forming a medical article comprising an implantable sponge, the method comprising the steps of:

(a) providing a mold comprising:

(i) a tube comprising a first open end, a second open end, and a wall extending therebetween, and (ii) an obstruction present in the second open end of the tube, wherein the obstruction is connected to the wall via at least two arms extending from the wall to the obstruction, (b) providing a slurry comprising water, (c) forcing the slurry through the tube from the first open end to the second open end and past the obstruction, thereby substantially filling the mold with slurry, and (d) lyophilizing the slurry present in the mold, thereby forming an implantable sponge in the form of a three-dimensional shape comprising a reservoir capable of holding a liquid, the reservoir defined by a sidewall and a recessed surface, wherein the recessed surface comprises a shape complementary to a shape of the obstruction, wherein the sidewall comprises a plurality of cutouts extending from a top surface of the sidewall toward the recessed surface, wherein the plurality of cutouts extends through the width of the sidewall.

2. The method according to claim 1, wherein the slurry further comprises acid-soluble collagen, collagen fibers, and mineral particles.

3. The method according to claim 1, wherein the slurry further comprises a mineral and the slurry has a solids content of from 10 wt % to 40 wt %.

4. The method according to claim 1, wherein the mold comprises from two to eight arms.

5. The method according to claim 1, wherein the obstruction comprises a convex surface.

6. A medical article formed by the method of claim 1.

7. The medical article according to claim 6, wherein the implantable sponge comprises natural polymer fibers.

8. The medical article according to claim 6, wherein the implantable sponge further comprises a mineral and the mineral is present as particles having an average particle diameter of from 0.05 mm to 2 mm.

9. The medical article according to claim 6, wherein the implantable sponge comprises from 50 wt % to 95 wt % of mineral and from 5 wt % to 50 wt % of collagen, based on the total weight of the implantable sponge in its dry state.

10. The medical article according to claim 6, wherein the implantable sponge comprises acid-soluble collagen, collagen fibers, and mineral particles.

11. The medical article according to claim 6, wherein the implantable sponge comprises native collagen fibers having an average fiber length of from 0.5 mm to 10 mm.

12. The medical article according to claim 6, wherein the medical article is in the general shape of a cylinder, elliptical cylinder, or polyhedron.

13. The medical article according to claim 6, wherein the sidewall comprises from two to eight cutouts.

14. The medical article according to claim 6, wherein the sidewall comprises a cutout that extends from the top surface of the sidewall in the direction of the recessed surface but does not reach the recessed surface.

15. The medical article according to claim 6, wherein the cutouts have a cross-sectional shape of a square, rectangle, trapezoid, portion of an ellipse, or portion of a circle.

16. The medical article according to claim 6, wherein the top surface of the sidewall meets an exterior surface of the sidewall at an angle of approximately 90 degrees.

17. The medical article according to claim 6, wherein the top surface of the sidewall meets an interior surface of the sidewall at an angle of approximately 90 degrees.

18. The medical article according to claim 6, wherein the recessed surface is concave.

19. The medical article according to claim 6, wherein the medical article is a bone void filler or suitable for use in filling a defect in bone.

*  *  *  *  *